(12) United States Patent
Decker et al.

(10) Patent No.: US 6,509,184 B1
(45) Date of Patent: Jan. 21, 2003

(54) **ALKALINE TOLERANT DEXTRANASE FROM *STREPTOMYCES ANULATUS***

(75) Inventors: Stephen R. Decker, Berthoud, CO (US); William S. Adney, Golden, CO (US); Todd B. Vinzant, Golden, CO (US); Michael E. Himmel, Littleton, CO (US)

(73) Assignee: Midwest Research Institute, Kansas City, MO (US)

( * ) Notice: Subject to any disclaimer, the term of this patent is extended or adjusted under 35 U.S.C. 154(b) by 0 days.

(21) Appl. No.: 09/379,665

(22) Filed: Aug. 24, 1999

(51) Int. Cl.[7] ............................. C12N 9/00; C12N 9/46; C12N 9/52; C12N 1/00; C12N 1/20
(52) U.S. Cl. .................. 435/211; 435/183; 435/220; 435/253.5; 435/253.6; 435/886
(58) Field of Search ................................. 435/183, 211, 435/252.1, 253.5, 822, 220, 253.6, 886

(56) References Cited

U.S. PATENT DOCUMENTS

| | | | |
|---|---|---|---|
| 3,702,805 A | 11/1972 | Ishibashi et al. | ............... 195/66 |
| 4,466,954 A | 8/1984 | Ichikawa et al. | ............. 424/50 |

*Primary Examiner*—Jon P. Weber
*Assistant Examiner*—Deborah K. Ware
(74) *Attorney, Agent, or Firm*—Paul J. White

(57) ABSTRACT

A process for production of an alkaline tolerant dextranase enzyme comprises culturing a dextran-producing microorganism *Streptomyces anulatus* having accession no. ATCC PTA-3866 to produce an alkaline tolerant dextranase, Dex 1 wherein the protein in said enzyme is characterized by a MW of 63.3 kDa and Dex 2 wherein its protein is characterized by a MW of 81.8 kDa.

9 Claims, 4 Drawing Sheets

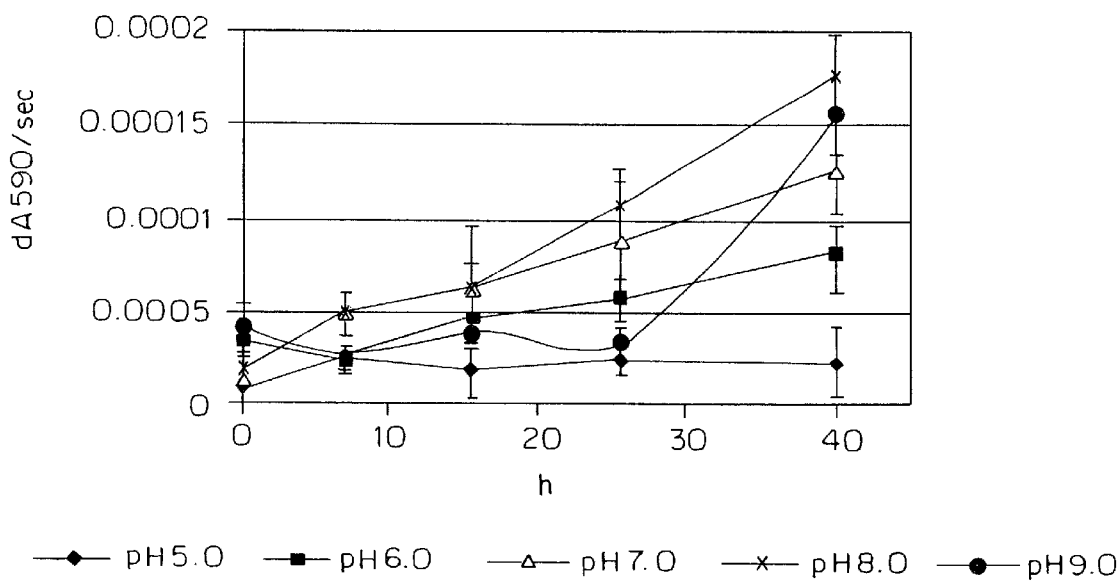
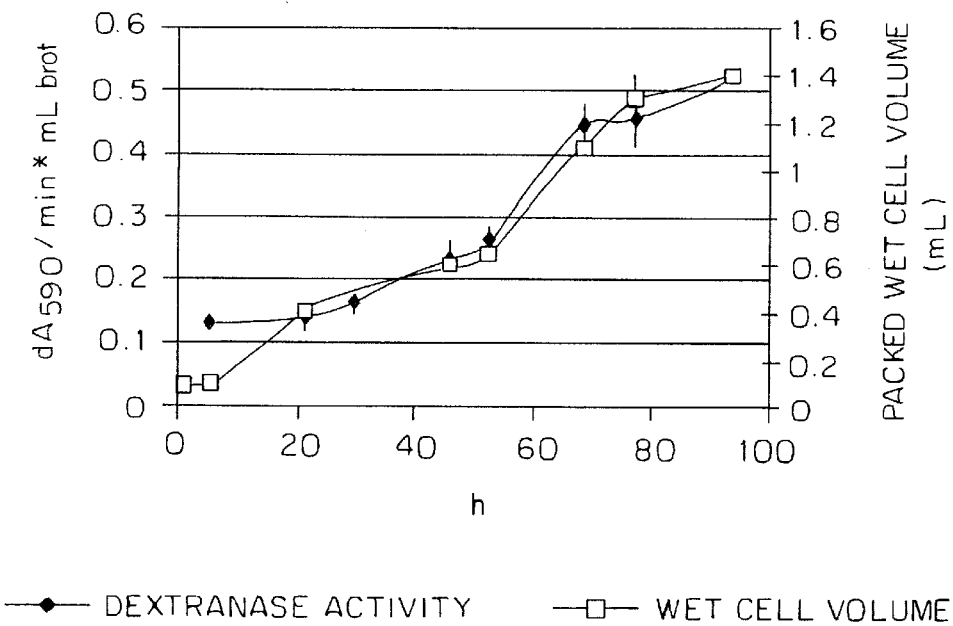

PNG1 DEXTRANASE ACTIVITY, 1.5 h

INITIAL RATES OF DEX1 AND DEX2

ALKALINE TOLERANT DEXTRANASE FROM *STREPTOMYCES ANULATUS*

CONTRACTUAL ORIGIN OF THE INVENTION

The United States Government has rights in this invention pursuant to Contract No. DE-AC36-99GO10337 between the United States Department of Energy and the National Renewable Energy Laboratory, a division of Midwest Research Institute.

FIELD OF THE INVENTION

This invention relates to new dextranases produced by Streptomyces anulatus. Two novel alkalotolerant dextranases were isolated from a single colony type that produced large clear halos in the blue dextran indicator pH 8.0. The organism was monocultured and identified by 16S rRNA sequencing as *Streptomyces anulatus*. Growth on dextran yielded two proteins active in hydrolyzing dextran, Dex 1 and Dex 2. Because enhanced activity lifetime after exposure to alkaline pH is important for enzymes used in detergent formulations, dextranases with these characteristics are of keen interest to the detergent industry.

BACKGROUND OF THE INVENTION

Dextran is an α(1→6) glucose polymer produced mainly by the bacteria *Leuconostoc mesenteroides* and some Lactobacillus and Streptococcus species as an extracellular carbohydrate storage compound. Dextran is currently used in such widely divergent products as food additives, cosmetics, blood plasma expanders, and as a chromatography support matrix. Dextranases are important commercial enzymes with applications in the food, chemical, dental, and detergent industries, with fungi being the primary production host.

One major industrial application of dextranases is the reduction of sliming in sugar production. Dextran production by Leuconostoc species during processing of sugar cane causes multiple problems, including fouling of filters, reduction in yield, poor crystallization, and low quality of the final product. Additional applications include prevention of *Streptococcus mutans* adherence to tooth enamel, cleaning biofilms from many surfaces, including contact lenses, and modification of dextran for food additives and support applications in cosmetics and chromatography media. Potential applications of dextranases include removal of biofilms from surgical implants and food processing equipment and utensils. Dextran and related polysaccharides are known constituents of microbial biofilms, which infiltrate wooden kitchen surfaces and tools, especially cutting boards. Enzymes degrading these polysaccharides are known as (EC 3.2.1.11) α-1,6-glucan 6-glucanohydrolase (α-1,6 glucanase or dextranase). It is reasonable to expect that formulation of cleaning products to contain dextranase enzymes could result in enhanced product performance on wood kitchen objects.

However, for effective performance in cleaners, dextranases must be able to resist the chemical and physical requirements of use. Therefore, it is important to identify new enzymes capable of withstanding high pH (at least pH 8.0) and elevated temperature (at least 60° C.) for a period of time consistent with exposure expected for liquid cleaner use (at least 15 min).

U.S. Pat. No. 4,466,954 discloses a dextranase-containing oral composition that comprises a dextranase enzyme and a stabilizing amount of an admixture comprising water-soluble salts of alkyl sulfates having 10, 12, 14 and 16 carbon atoms in the alkyl chain; however, the dextranase produced is from the genus Chaetomium which is a fungi.

An improved process for the production of dextranase is disclosed in U.S. Pat. No. 3,702,805, wherein said process comprises culturing a dextranase-producing microorganism selected from the genera Chaetomium, Humicola, Sporotrichum, Anixiella, Macrosporium, Streptomyces, Gibberella, Gloeosporium and Glomerella, particularly *Chaetomium spirale, Chaetomium gracile, Sporotrichum asteroides*, or *Gibberellafujikuroi* in a fermentation medium and recovering from said medium the dextranase which accumulates therein. This patent does not disclose an isolate from *Streptomyces anulatus*, and contains no information pertaining to the composition of matter of the dextranases.

None of the prior art references disclose the invention Dex 1 and Dex 2 alkaline tolerant dextranase species in a broth culture of *Streptomyces anulatus*.

SUMMARY OF THE INVENTION

The present invention provides two novel alkalotolerant dextranases isolated during a directed screening operation in which soil, water, and biomass samples were collected from the Pawnee National Grasslands in Northeastern Colorado and screened on blue dextran plates for activity to provide an observed single colony type that consistently produced large clear halos in the blue dextran indicator, even at pH 8.0. The organism was monocultured and identified by 16S rRNA sequencing as *Streptomyces anulatus*.

A further aspect of the invention is to provide growth on dextran which yields two proteins active in hydrolyzing dextran, Dex 1 and Dex 2, wherein Dex 1 has a MW of 63.3 kDa, a pH range of 5.0 to 9.5 and a temperature optimum of 40° C. and Dex 2 has a MW of 81.8 kDa, with a pH range of 5.0 to 9.5 and a temperature optimum of 5° C.

Another aspect of the invention is to provide enzymes that retain >50% activity from pH 5.3 to 9.3 after three hours, with 100% retention from 6.0 to 8.5 after three hours.

Yet another aspect of the invention is to provide an active protein Dex 1 characterized by sequencing

```
SEQ ID NO:10  Asn Trp Asp Asn Trp Asn Ala Trp Gly Pro Gly Gly Asn Pro Asp Pro Gly;
              1               5                  10                 15

SEQ ID NO:11  Gly Gly Gly Pro Asn Arg Ala Ile His Thr Glu Pro Arg Asn Ser; and
              1               5                  10                 15

SEQ ID NO:12  Glu Ile Ile Tyr Phe Arg Pro Gly Thr Tyr
              1               5                  10
```

An additional aspect of the invention is to provide the active proteins Dex 1 and Dex 2 with enhanced activity lifetime after exposure to wide-ranging conditions of pH (especially excursions to alkaline pH) as enzymes for detergent formulations, as dextranases with these characteristics are of keen interest to industry.

BRIEF DESCRIPTION OF THE DRAWINGS

FIG. 1 is a graph of the rate of dextranase activity, wherein dextranase production is measured by plotting the rate of activity of culture broth against time for each of five pH cultures.

FIG. 2 is a graph showing dextranase production, wherein dextranase production was monitored over the course of the fermentation using a Cary 3 dual beam thermostated spectro-photometer with a stirring multi-cell attachment.

DESCRIPTION OF THE PREFERRED EMBODIMENTS

Figure 3:
FIG. 3 shows a blue dextran plate, wherein blue dextran agar showing dye builds up at the edges of the clearing zones around *Streptomyces anulatus* colonies, and in which there is an absence of any other colony type on the initial isolation plate.

The invention is the development of two novel alkalotolerant dextranases isolated during a directed screening operation of soil, water, and biomass samples collected from the Pawnee National Grasslands in Northeastern Colorado and screened on blue dextran plates for activity.

A single colony type was observed that consistently produced large clear halos in the blue dextran indicator even at a pH of up to 8.0. The organism was monocultured and identified by 16S rRNA sequencing of *Streptomyces anulatus*. Growth on dextran yielded two proteins active in hydrolyzing dextran, Dex 1 and Dex 2.

Dex 1 was found to have a MW of 63.3 kDa, a pH range of from about 5.0 to about 9.5, and a temperature optimum of about 40° C.

Dex 2 was found to have a MW of 81.8 kDa, with a pH range of from about 5.0 to about 9.5 and a temperature optimum of about 50° C.

The Dex 1 and Dex 2 enzymes retained >50% activity from a pH range of from about 5.3 to about 9.3 after 3 hours, with 100% retention from a pH of from about 6.0 to about 8.5 after 3 hours.

From our knowledge of known dextranases, as is shown in Table 1 below, no alkalophilic dextranases have been reported.

TABLE 1

| SwissProt code | Source Microorganism | Enzyme mw | Optima Tem | Optima pH | Enzyme pI |
|---|---|---|---|---|---|
| DEXT_ARTGO | *Arthrobacter globiformis* | 68,069 | / | | 5.19 |
| DEXT_ARTXT | *Arthrobacter sp.* (Str. CB-8)* | 66,645 | | | 5.24 |
| DEXT_PENMI | *Penicillium minioluteum*** | 62,510 | | | 5.03 |
| DEXT_STRDO | *Streptococcus downei* | 140,089 | | | 4.35 |
| DEXT_STRMU | *Streptococcus mutans* | 94,538 | | | 4.94 |
| DEXT_STRSL | *Streptococcus salivarius* | 84,087 | | | 4.52 |
| | *Penicillium notatum* D-1 | 55,800 | 50 | 4.8 | 4.9 (experimental) |
| | D-2 | 50,100 | | | 4.75 (experimental) |
| | *Lipomyces starkeyi* | | 55 | 5.5 | |
| | *Penicillium lilacinum* | 26,500 | | | |
| | *Thermoanaerobacter spp.* AB11Ad | | 70 | 5–6 | |
| | Rt364 | 140,000 | 80 | 5.5 | |
| | *Streptococcus suis* | 62,000 | | | |
| | *Sporothrix schenckii* | 79,000 | | 5.0 | |
| | *Streptococcus sobrinus* (*E. coli* expressed) | 160,000–260,000 | 39 | 5.3 | 3.56, 3.6, 3.7 (experimental) |
| | *Chaetomium gracile* | | 55 | ~5.0 | |
| | *Chaetomium spirale* | | | ~5.0 | |
| | *Gibberella fujikuroi* | | | ~5.0 | |
| | *Humicola grisea* | | | ~5.0 | |
| | *Sporotrichum asteroides* | | | ~5.0 | |
| | *Penicillium roquefortii* | | | ~5.0 | |
| | *Aspergillus fumigatus* | | | ~5.0 | |
| | *Streptomyces cinnamonensis* | | | ~5.0 | |
| None | *Trichoderma harzianum**** | ca. 50,000 | | | 5.60 (experimental) |

*#5,306,639. #5,637,491. *#5,770,406 (pH opt 5.0; Topt = 30–40° C.)

EXAMPLE

Materials and Methods

Microorganism. *Streptornyces anulatus* was isolated on blue dextran indicator plates from soil sample taken from a chicken coop situated on an abandoned homestead site in the Pawnee National Grasslands. The microorganism was cultured at pH 7.1, 28° C. and was identified by 16S rRNA sequence analysis as *Streptomyces anulatus* at MIDI Labs (Newark, Del.). Enzyme production occurs optimally at pH 8.0 in submerged fermentation (FIG. 1) with dextranase activity closely following cell mass production (FIG. 2). The microorganism identified as *Streptomyces anulatus* has been deposited at ATCC (American Type Culture Collection), P.O. Box 1549, Manasass, Va. 20108, on Nov. 16, 2001, and having accession number ATCC PTA-3866.

Media and culture conditions. The basic media consisted of: $(NH_4)_2SO_4$ 11.7 g/L, $MgSO_4.7H_2O$ 0.6 g/L, $K_2HPO_4$ 8.7 g/L, NaCl 0.6 g/L, $CaCl_2.2H_2O$ 0.05 g/L, yeast extract 5.0 g/L, and trace elements ($FeSO_4.7H_2O$ 0:5 g/L, $MnSO_4.H_2O$ 0.16 g/L, $ZnSO_4.7H_2O$ 0.14g/L, $CoCl_2.6H_2O$ 0.37g/L) 1.0 mL/L. Dextran (5.0 g/L) was used as a carbon source/inducer and Blue Dextran (0.05 g/L) was incorporated as an enzyme activity indicator in the initial isolation and screening plates. Fermentation optimization for pH was carried out in New Brunswick BioFlo III 1.0 L fermenters. The optimal pH for enzyme production was determined over the range of pH 5.0 to 9.0 and measured by plotting the rate of enzyme activity produced against time of culture growth for each pH measured. Optimum enzyme production temperature was determined by looking at cell growth rates over a temperature range of 20–37° C. For enzyme production, the organism was cultured in 100 mL liquid medium and sequentially transferred to 400 mL, 10 L and finally to a 100 L culture in a 150 L capacity production fermenter (New Brunswick ML4100) which was run at 28° C., 200 rpm, with $dO_2$ maintained at 20% via airflow regulation and pH control at pH 7.6. Dextran was fed at 42 h (100 g) and 68 h (200 g). The culture harvested at 96 h.

Activity measurements and enzyme characterization. Enzyme activity was measured using an insoluble dyed, cross-linked dextran (AZCL-Dextran, Megazyme, Inc.) and measuring $A_{590}$ in a Cary3 UV/VIS thermostated spectrophotometer using a 3 mL stirred cell containing 0.25g/L AZCL-Dextran in 20 mM Tris pH 8.0 at 40° C. The rate of activity was measured over ten minutes as the rate of increase in $A_{590}$ over time. For enzyme pH and temperature optima, all conditions remained the same except for the parameter being measured. To follow activity, 150 µL of 0.3% AZCL-Dextran in 20 mM Tris pH 8.0 was incubated with 50 µL of sample at 40° C. in a microtiter plate well. Dye release was determined by visual examination. The molecular weights of the proteins were determined by SDS-PAGE using a Novex system 14% tris-glycine 1.0 mm gel run at 20 mA constant, 110 min under reducing conditions. Sigma molecular weight markers were used as standards in the molecular weight determination. Gels were stained with a Novex Colloidal Coomassie staining kit. Amino acid sequences for Dex 1 were determined at the University of Virginia Biomolecular Research Facility. The protein was alkylated and then digested with lysyl peptidase. The peptides were separated on a C18 BPLC column and then sequenced by Edman degradation.

Enzyme purification. One hundred liters of culture broth from *Streptomyces anulatus* was clarified using a Cepa continuous flow centrifuge and concentrated from 100 L to 13.3 L with an Amicon DC30 diafiltration unit with a 10kDa MWCO hollow fiber cartridge. After further clarification by centrifugation, 50 mL of the concentrated culture broth was diluted with 3 volumes of 20 mM Bis-Tris-Propane, pH 9.0 and loaded onto a 6 mL Phariacia ReSourceQ column. The unbound flow through was collected and brought to 130 mS/cm with $(NH_4)_2SO_4$ and loaded onto a 20 mL Pharmacia Phenyl Sepharose column and eluted with a complex decreasing $(NH_4)_2SO_4$ gradient (1.0→0.0 M) in 20 mM Tris buffer pH 8.2 over 20 column volumes.

Dex 1 and Dex2 eluted as distinct peaks at 0.7 M and 0.4 M ammonium sulfate, respectively. The two active peaks were concentrated and further purified on a Pharmacia SuperDex200 size exclusion column.

Results and Discussion

Screening of soil/biomass/water samples from the Pawnee National Grasslands sites gave a multitude of colony types on the variety of media employed, but only a single dextran hydrolyzing colony type on Blue Dextran plates (FIG. 3). *Streptomyces anulatus* grew as the sole organism on one of the Blue Dextran plates inoculated with soil from the homestead chicken coop. It sporulated readily, forming soft, white, powdery spores, and appeared to be a streptomycete under macro- and microscopic examination. The 16s RNA sequence data confirmed this. The organism showed 100% homology in the first 500 bps of the 16s RNA to *Streptomyces anulatus*. The ability of the isolated organism to actively exclude any other organism from the plate has been attributed to the production of puromycin by *S. anulatus*.

The organism was originally isolated at room temperature. Growth at 28, 30, and 37° C. was also monitored, with growth and enzyme production peaking at 28 to 30° C. The culture pH optimum for enzyme production (FIG. 1) was determined to be pH 8.0. Lower pH values yielded significantly less enzyme activity as demonstrated by the comparison of enzyme rates from each pH over time. Interestingly, the culture grown at pH 9.0 showed a long lag phase in getting started, but presented a rapid rise in enzyme production once the cells had adapted to the high pH and started growing. The correlation between cell mass and enzyme production was also indicated in the 100 L culture where enzyme production closely followed biomass generation (FIG. 2).

Figure 4:
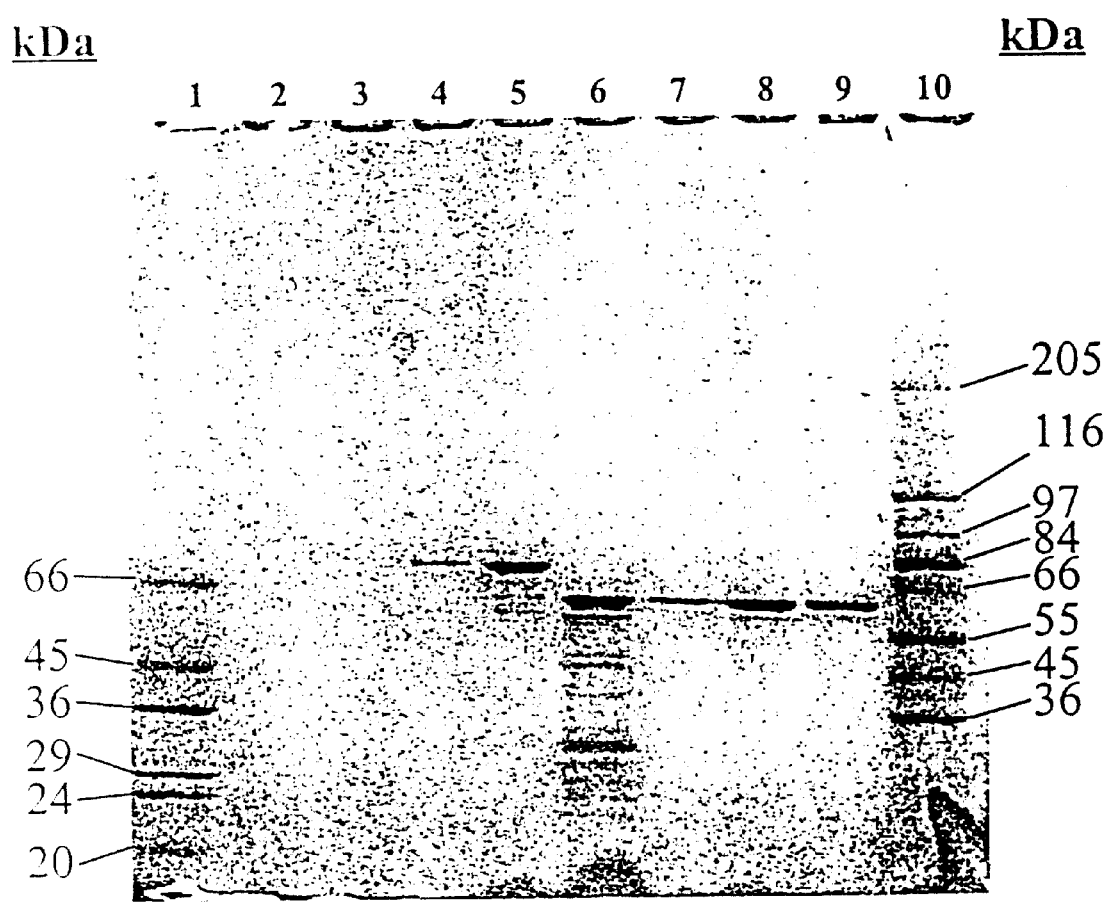
FIG. 4 shows an SDS-PAGE molecular weight determination of Dex 1 and Dex 2 determined on a Novex 14% Tris-Glycine gel run at 20 mA constant for 110 minutes.

Purification of the enzymes by column chromatography presented a difficult challenge, as the proteins did not bind to cation exchange at pH 5.0. Also, the proteins did not readily bind to anion exchange columns, except at pH 9.0 under extremely low salt concentrations. Fortunately, the anion exchange bound most of the other proteins and allowed the unbound dextranases to be separated on a phenyl sepharose HIC column. Final purification was achieved by size-exclusion on a SuperDex200 column. This was carried out only for protein characterization, as the application of dextranases to a dextran-based column was deemed "risky". The SuperDex purified proteins were used for molecular weight determination by SDS-PAGE (FIG. 4). For all other enzyme characterization, the HIC fractions were used. The molecular weights were determined to be 63.3 and 81.8 kDa for Dex 1 and Dex2, respectively.

Figure 5:
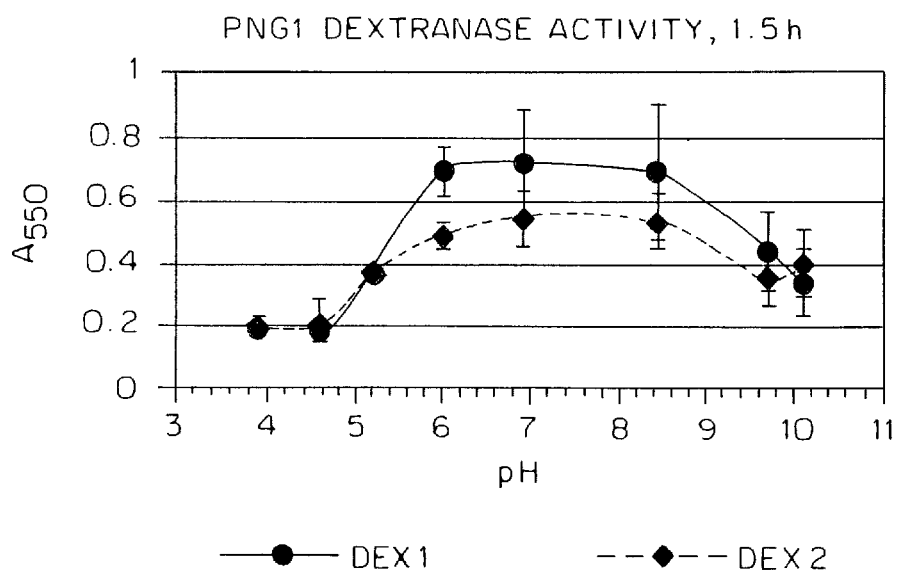
FIG. 5 is a graph showing the pH optimum for enzyme activity was broad for both Dex 1 and Dex 2 enzymes.
Figure 6:
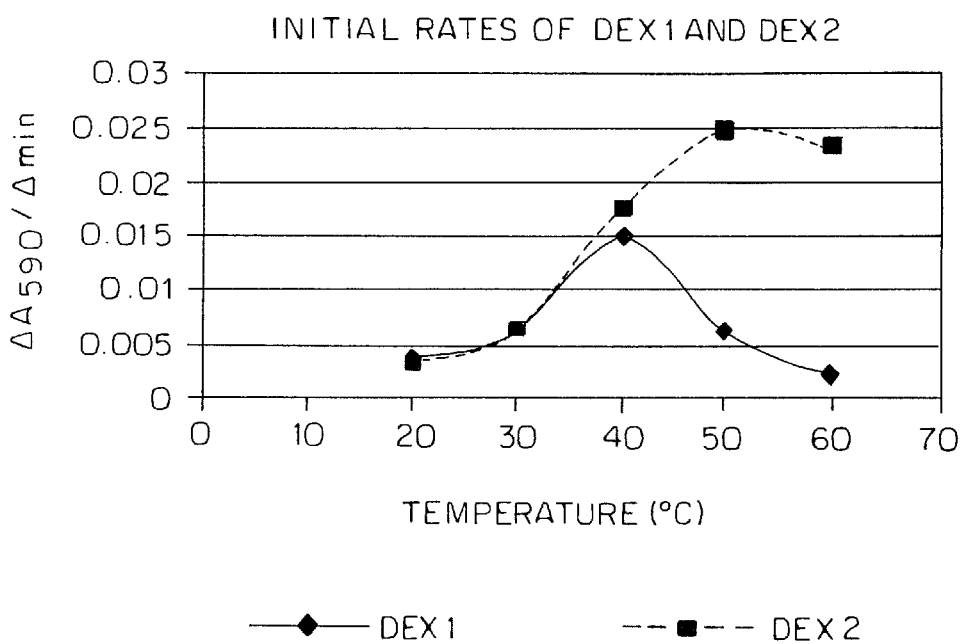
FIG. 6 is a graph showing temperature optima of the enzymes Dex 1 and Dex 2.

The pH optimum for enzyme activity was broad for both enzymes (FIG. 5). For Dex 1, the pH range for 50% or greater activity was about pH 5.1 to 10.1. The range of Dex2 was slightly narrower, from pH 4.8 to 9.5. This activity range was measured over 1.5 hours, so it indicates the initial stability and activity of the enzymes. Long-term stability was not measured. Both enzymes also exhibit broad pH optima, with Dex 1 and Dex 2 having pH optima of pH 7.0 to 8.0 and pH 6.0 to 8.0, respectively. Similarly, temperature optima of the enzymes were also determined (FIG. 6). Dex 1 has a temperature range for 50% or greater activity of 30° C. to 50° C. and for Dex2 this range is 35° C. to 75° C. Again, these activities are for initial activity and temperature stability was not measured. The temperature optima for Dex 1 and Dex 2 were 40° C. and 50° C., respectively. These values are significant, as most known dextranases exhibit low pH and moderate temperature optima.

The pH data is especially important for applications requiring activity at alkaline pH, such as detergent formulations. These data are summarized in Table 2.

TABLE 2

Temperature and pH Characteristics for Dex 1 and Dex 2

| Enzyme | $T°_{opt}$ | $pH_{opt}$ | T° range[1] | pH range[2] |
|---|---|---|---|---|
| Dex1 | ~40° C. | 7.0–8.0 | 30–50° C. | 5.1–10.1 |
| Dex2 | ~50° C. | 6.0–8.0 | 35–75+° C. | 4.8–9.5+ |

[1]Range is defined as lower and upper temperature giving 50% of the optimal activity.
[2]Range is defined as lower and upper pH giving 50% of optimal activity.

Tolerance for alkaline pH is an important characteristic for enzymes incorporated into detergent formulations. Although the pI for the dextranases has not been determined, the binding characteristics on ion exchange chromatography media and the elevated pH tolerance and optima indicate an alkaline pI. This is supported by preliminary IEF data (not shown) suggesting alkaline isoelectric points for both proteins.

From analysis of the protein sequence data, Dex 1 belongs to Family 49 of the glycosyl hydrolase families. Other members of this group include dextranases from *Penicillium minioluteum, Arthrobacter globifonnis*, and another Arthrobacter species. Pairwise alignnient of the Dex 1 protein sequence fragments with these known dextranases indicated a 64.3% identity to the two *Arthrobacter dextranases* (DEXT_ARTGO and DEXT_ARTSP), placing Dex 1 in Family 49. Importantly, the pairwise percent identity with the *Penicillium dextranase* was only 28.6%, even though both proteins are apparently in the same glycosyl hydrolase family as shown in Table 3 (See Table 3).

TABLE 3

Comparison of Dex 1 sequences with Family 49 dextranases

*Arthrobacter globiformis*

SEQ ID NO: 1  Asn Trp Asp Ser Trp Asn Ala Trp Lys Ser Ala Pro;
              1               5                   10

SEQ ID NO: 2  Glu Ala Glu Gly Asn Arg Pro Ile His Thr Glu Pro Arg Asn Ser; and
              1               5                   10                  15

SEQ ID NO: 3  Glu Ile Ile Tyr Phe Arg Pro Gly Thr Tyr
              1               5                   10

*Arthrobacter spp.*

SEQ ID NO: 4  Asn Trp Glu Asn Trp Asn Ala Trp Lys Ser Ala Pro;
              1               5                   10

SEQ ID NO: 5  Glu Ala Ala Gly Asn Arg Pro Ile His Thr Glu Pro Arg Asn Ser; and
              1               5                   10                  15

SEQ ID NO: 6  Glu Ile Ile Tyr Phe Arg Pro Gly Thr Tyr
              1               5                   10

*Penicillium minioleuteum*

SEQ ID NO: 7  Asn Ile Asp Gly Ser Tyr Trp Gly Glu Trp Gln Ile Ser;
              1               5                   10

SEQ ID NO: 8  Val Thr Ser Gly Gly Ser Val Val Gly Val Glu Pro Thr Asn Ala; and
              1               5                   10                  15

SEQ ID NO: 9  Ser Ile Leu Tyr Phe Pro Pro Gly Val Tyr
              1               5                   10

Dex 1

SEQ ID NO: 10 Asn Trp Asp Asn Trp Asn Ala Trp Gly Pro Gly Gly Asn Pro Asp Pro Gly;

TABLE 3-continued

Comparison of Dex 1 sequences with Family 49 dextranases

|   | 1 |   |   |   | 5 |   |   |   |   | 10 |   |   |   |   |
|---|---|---|---|---|---|---|---|---|---|----|---|---|---|---|
| SEQ ID NO: 11 | Gly | Gly | Gly | Pro | Asn | Arg | Ala | Ile | His | Thr | Glu | Pro | Arg | Asn | Ser; and |
|   | 1 |   |   |   | 5 |   |   |   |   | 10 |   |   |   |   | 15 |
| SEQ ID NO: 12 | Glu | Ile | Ile | Tyr | Phe | Arg | Pro | Gly | Thr | Tyr |
|   | 1 |   |   |   | 5 |   |   |   |   | 10 |

Since these families are based on structural similarities and not sequence homology, this is not unexpected. Homology between the Arthrobacter dextranases and the Penicillium dextranase is also low, around 35%. These sequence alignment experiments indicate that Dex 1 is a unique protein and thus, a new composition of matter.

As can be seen from FIG. 1, dextranase production is measured by plotting the rate of activity of culture broth against time of culture for each 5 pH cultures. Dextranase activity was determined using a Cary 3 dual beam thermostated spectrophotometer with a stirring multi-cell attachment. Each time point sample was run in triplicate for each pH against a blank with no enzyme. The substrate was 0.025% (w/v) AZCL-Dextran. The activity was monitored for dye release at 590 nm over 10 minutes.

In FIG. 2, dextranase production was monitored over the course of using a Cary 3 dual beam thermostated spectrophotometer with a stirring multi-cell attachment. Each sample was run in triplicate for enzyme activity against a blank with no enzyme. The substrate was 0.025% (w/v) AZCL-Dextran. The activity was monitored for dye release at 590 nm over 10 minutes. Cell mass was measured as packed cell volume of 15 mL broth samples centrifuged and measured in graduated 15 mL conical tubes.

The MWs of Dex 1 and Dex 2 are shown in FIG. 4 and were determined on a Novex 14% Tris-Glycine gel run at 20 mA constant for 110 minutes. The gel was stained with Novex Colloidal Coomassie Blue. Lane 1 Sigma Low Range molecular weight markers, Lanes 2–3 empty , Lane 4 and 5 Dex 2, Lane 6 partially purified Dex 1, Lane 7–9 Dex 1, Lane 10 Sigm High Range molecular weight markers.

The pH optima and range for Dex 1 and Dex 2 are shown in FIG. 5, and were determined using a Cary 3 dual beam thermostated spectrophotometer with a stirring multi-cell attachment. Each pH was run in duplicate for each enzyme prep (Dex 1 or Dex 2) against a blank with no enzyme. The substrate was 0.025% (w/v) AZCL-Dextran. The activity was monitored for dye release at 590 nm over 10 minutes. The pH range covered 3.9 to 10.1 using a Tris-acetate-citrate buffer system adjusted to constant ionic strength with NaCl. The rate of dye release ($A_{590}$) was plotted against pH.

FIG. 6 shows the temperature optima and range for Dex 1 and Dex 2 determined using a Cary 3 dual beam thermostated spectrophotometer with a stirring multi-cell attachment. Each temperature was run in duplicate for each enzyme prep (Dex 1 or Dex 2) against a blank with no enzyme. The substrate was 0.025% (w/v) AZCL Dextran. The activity was monitored for dye release at 590nm over 10 minutes. The temperature range covered 20–60° C. The rate of dye release ($A_{590}$) was plotted against temperature.

We claim:

1. A process for production of an alkaline tolerant dextranase enzyme comprising culturing a dextranase-producing microorganism *Streptomyces anulatus* having accession no. ATCC PTA-3866 to produce an isolated alkaline tolerant dextranase enzyme.

2. The process of claim 1, wherein said dextranase-producing microorganism is cultured at a pH of about 7.1 and a temperature of about 28° C.

3. The process of claim 2 wherein said isolated alkaline tolerant dextranase enzyme produced is Dex 2, and said enzyme has a MW of 81.8 kDa.

4. The process of claim 3 wherein said Dex 2 has a pH range of about 5.0 to about 9.5 and a temperature optimum of about 50° C.

5. The process of claim 1, wherein said isolated alkaline tolerant dextranase enzyme produced is Dex 1, wherein said enzyme has a MW of 63.3 kDa; and wherein internal peptide fragments coding for Dex 1 are selected from the group consisting of 6. The process of claim 5 wherein said Dex 1 has a pH range of about 5.0 to about 9.5 and a temperature optimum of about 40° C.

7. The process of claim 1 wherein said isolated alkaline tolerant dextranase enzymes retains greater than 50% activity at a pH of from about 5.0 to about 9.5 after three hours, and further has a 100% retention of activity at a pH of from about 7.0 to about 8.0 after three hours.

8. An isolated Dex 1 alkaline and thermal tolerant dextranase enzyme produced from a biologically pure microorganism *Steptomyces anulatus* having accession no. ATCC PTA-3866, wherein said enzyme has a MW of 63.3 kDa, a pH range from about 5.0 to about 9.5, a temperature optimum of about 40° C.; and wherein internal peptide fragments coding for Dex 1 are selected from the group consisting of:

```
SEQ ID NO:10 Asn Trp Asp Asn Trp Asn Ala Trp Gly Pro Gly Gly Asn Pro Asp Pro Gly;
                 1               5                   10                  15

SEQ ID NO:11 Gly Gly Gly Pro Asn Arg Ala Ile His Thr Glu Pro Arg Asn Ser;
                 1               5                   10                  15

SEQ ID NO:12 Glu Ile Ile Tyr Phe Arg Pro Gly Thr Tyr and mixtures thereof.
                 1               5                   10
```

SEQ ID NO:10  Asn Trp Asp Asn Trp Asn Ala Trp Gly Pro Gly Gly Asn Pro Asp Pro Gly;
              1               5                   10              15

SEQ ID NO:11  Gly Gly Gly Pro Asn Arg Ala Ile His Thr Glu Pro Arg Asn Ser;
              1               5                   10              15

SEQ ID NO:12  Glu Ile Ile Tyr Phe Arg Pro Gly Thr Tyr and mixtures thereof.
              1               5                   10

9. An isolated Dex 2 alkaline and thermal tolerant dextranase enzyme produced from a biologically pure microorganism *Streptomyces anulatus* wherein said enzyme having accession no. ATCC PTA-3866, has a MW of 81.8 kDa, a pH range of from about 5.0 to about 9.5, and a temperature optimum of about 50° C.

* * * * *

SEQUENCE LISTING

```
<160> NUMBER OF SEQ ID NOS: 12

<210> SEQ ID NO 1
<211> LENGTH: 12
<212> TYPE: PRT
<213> ORGANISM: Arthrobacter globiformis

<400> SEQUENCE: 1

Asn Trp Asp Ser Trp Asn Ala Trp Lys Ser Ala Pro
1               5                   10

<210> SEQ ID NO 2
<211> LENGTH: 15
<212> TYPE: PRT
<213> ORGANISM: Arthrobacter globiformis

<400> SEQUENCE: 2

Glu Ala Glu Gly Asn Arg Pro Ile His Thr Glu Pro Arg Asn Ser
1               5                   10                  15
```

```
<210> SEQ ID NO 3
<211> LENGTH: 10
<212> TYPE: PRT
<213> ORGANISM: Arthrobacter globiformis

<400> SEQUENCE: 3

Glu Ile Ile Tyr Phe Arg Pro Gly Thr Tyr
1               5                   10

<210> SEQ ID NO 4
<211> LENGTH: 12
<212> TYPE: PRT
<213> ORGANISM: Arthrobacter sp.

<400> SEQUENCE: 4

Asn Trp Glu Asn Trp Asn Ala Trp Lys Ser Ala Pro
1               5                   10

<210> SEQ ID NO 5
<211> LENGTH: 15
<212> TYPE: PRT
<213> ORGANISM: Arthrobacter sp.

<400> SEQUENCE: 5

Glu Ala Ala Gly Asn Arg Pro Ile His Thr Glu Pro Arg Asn Ser
1               5                   10                  15

<210> SEQ ID NO 6
<211> LENGTH: 10
<212> TYPE: PRT
<213> ORGANISM: Arthrobacter sp.

<400> SEQUENCE: 6

Glu Ile Ile Tyr Phe Arg Pro Gly Thr Tyr
1               5                   10

<210> SEQ ID NO 7
<211> LENGTH: 13
<212> TYPE: PRT
<213> ORGANISM: Penicillium minioluteum

<400> SEQUENCE: 7

Asn Ile Asp Gly Ser Tyr Trp Gly Glu Trp Gln Ile Ser
1               5                   10

<210> SEQ ID NO 8
<211> LENGTH: 15
<212> TYPE: PRT
<213> ORGANISM: Penicillium minioluteum

<400> SEQUENCE: 8

Val Thr Ser Gly Gly Ser Val Val Gly Val Glu Pro Thr Asn Ala
1               5                   10                  15

<210> SEQ ID NO 9
<211> LENGTH: 10
<212> TYPE: PRT
<213> ORGANISM: Penicillium minioluteum

<400> SEQUENCE: 9

Ser Ile Leu Tyr Phe Pro Pro Gly Val Tyr
1               5                   10

<210> SEQ ID NO 10
<211> LENGTH: 17
```

```
<212> TYPE: PRT
<213> ORGANISM: DEX 1

<400> SEQUENCE: 10

Asn Trp Asp Asn Trp Asn Ala Trp Gly Pro Gly Gly Asn Pro Asp Pro
1               5                   10                  15

Gly

<210> SEQ ID NO 11
<211> LENGTH: 15
<212> TYPE: PRT
<213> ORGANISM: DEX 1

<400> SEQUENCE: 11

Gly Gly Gly Pro Asn Arg Ala Ile His Thr Glu Pro Arg Asn Ser
1               5                   10                  15

<210> SEQ ID NO 12
<211> LENGTH: 10
<212> TYPE: PRT
<213> ORGANISM: DEX 1

<400> SEQUENCE: 12

Glu Ile Ile Tyr Phe Arg Pro Gly Thr Tyr
1               5                   10
```